United States Patent [19]
Perez et al.

[11] Patent Number: 5,646,400
[45] Date of Patent: Jul. 8, 1997

[54] CORROSION DETECTING AND MONITORING METHOD AND APPARATUS

[75] Inventors: Ignacio M. Perez, Yardley; Vinod S. Agarwala, Warminster, both of Pa.

[73] Assignee: The United States of America as represented by the Secretary of the Navy, Washington, D.C.

[21] Appl. No.: 502,661

[22] Filed: Jul. 14, 1995

[51] Int. Cl.$^6$ ........................................... G01J 3/18
[52] U.S. Cl. ..................... 250/227.18; 250/226; 385/12
[58] Field of Search ................. 250/227.14, 227.18, 250/227.19, 227.23, 227.27, 226; 356/32; 385/12

[56] References Cited

U.S. PATENT DOCUMENTS

| | | | |
|---|---|---|---|
| 5,319,435 | 6/1994 | Melle et al. | 250/227.18 |
| 5,493,390 | 2/1996 | Varasi et al. | 250/227.18 |
| 5,513,913 | 5/1996 | Ball et al. | 250/227.18 |

OTHER PUBLICATIONS

R. E. Johnson, V. S. Agarwala, *Material Performance*, p. 25, Apr. 1994.
A. W. Snyder, J. D. Love, "Optical Waveguide Theory", Chapman and Hall pub., 1983, p. 460.
S. M. Melle K. Liu, R. M. Measures, *Applied Optics*, vol. 32, p. 3601 (1993).
I. Perez, V. Agarwala, W. R. Scott, "Bragg Grating Corrosion Sensor", Proceedings of the 19th Progress in Quantitative Nondestructive Evaluation, Iowa State U., Jul.–Aug. 1994, presentation on 31 Jul. 1994.

*Primary Examiner*—Edward P. Westin
*Assistant Examiner*—Kevin Pyo
*Attorney, Agent, or Firm*—Susan E. Verona; Ron Billi

[57] ABSTRACT

A nondestructive method and apparatus for optical detection and monitoring corrosion in structures normally inaccessible to light and observation. An optical fiber coated with a corrosion sensitive compound is embedded in the structure. Tapped Bragg gratings of different Bragg periods are spaced along the fiber and refract a narrow bandwidth component of a broad beam light pulse transmitted through the fiber. Due to corrosion, the refracted components are reflected by the compound and their amplitudes are detected and displayed for each narrow bandwidth.

12 Claims, 2 Drawing Sheets

CORROSION DETECTING AND MONITORING METHOD AND APPARATUS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates generally to corrosion and material damage detection; and more particularly to a nondestructive method and apparatus for optical detection and monitoring corrosion and material degradation in metal and composite structures which are generally inaccessible to light and visual inspection.

A heavy toll on material and maintenance costs on military as well as commercial aircraft can be attributed to the severity of the environment in which they operate. Under the influence of environmental effects or corrosion, susceptibility to stress-corrosion cracking and corrosion fatigue of critical aircraft structural materials (steels and aluminum) increase by a factor greater than ten and significantly reduce the useful life of aircraft. Even newer aircraft which use advanced materials such as graphite/epoxy composites are susceptible to such effects. Frequently, they are detected too late for any simple measure to be taken to repair damaged parts. Occasionally, if the corrosion or environmental effects were not discovered in time, the results could be catastrophic.

As current fleets of aircraft age without new aircraft entering a fleet inventory, the degrading effects of corrosion become more critical in terms of maintenance, readiness and safety. Flying aircraft near their expected useful life might actually be well beyond their safe life. Due to limited resources, some aircraft are not retired at their original expected lives but are reconditioned to fly beyond that time. Consequently, frequent inspections, preventive maintenance, and repairs require older aircraft to be removed periodically from service for costly and extended periods of time. In many cases, it is necessary to remove the aircraft's skin to access parts for inspection further adding to cost and down-time.

All of these considerations indicate that early detection and quantification of corrosion is extremely important, especially for carrier-based Navy aircraft which are exposed at sea to extremely corrosive environments.

Extensive studies in the area of corrosion detection and prevention have been carried out in the laboratory. In connection with these studies, electrochemical sensors (current) and optical (color) sensor for detecting early signs of corrosion have been investigated.

Electrochemical sensors are either incorporated in coatings or installed in a structure to produce signals when there is corrosion or damage, and before the effects become too severe. The sensing elements are bimetallic galvanic ultrathin-film devices fabricated on a polymeric film to generate a current when exposed to moisture.

Optical sensors, on the other hand, require reduction-oxidation (redox) chemicals which produce a change in an optical property such as a color or fluorescence when exposed to visible or ultraviolet light. However, the choice of inspection sites in structures for optically detecting corrosion is greatly limited because they must be accessible to both light and observation at the sensors. For instance, optical changes produced by redox reactions and/or corrosion in lap joints, under protective coatings or paint and on the backside of aircraft skin are particularly difficult to observe.

SUMMARY OF THE INVENTION

Accordingly, it is an object of the present invention to provide a nondestructive method and apparatus for optical detection and monitoring of corrosion and environmental effects in structures which are normally inaccessible to light and observation.

Another object is to provide an optical sensor which will detect corrosion in lap joints, under paint and on the backside of the skin of an aircraft or like structure.

Still another object is to provide an corrosion monitoring system in which a single optic fiber can be installed in critical aircraft structures to provide early detection and cumulative quantification of corrosion at multiple sites within the structure.

A still further object is to provide a sensing element which is small, lightweight, immune to electromagnetic interference and corrosion, and which can be easily embedded in or surface mounted on a structure.

Briefly, these and other objects and novel features of the invention are accomplished in a corrosion detection and monitoring system utilizing an optical fiber coated with a corrosion sensitive compound suitable for embedment in structure such as lap joints, under paint primers and topcoats, and on the backside of aircraft skin. Tapped Bragg gratings of different Bragg periods formed in the optical fiber at spaced intervals each tap off a unique "signature" having a narrow wavelength component of a broad beam light input pulse transmitted through the optical fiber. The tapped components scatter light into an optically sensitive compound at respective grating sites, and any change in a specified optical property of the coating, such as color or fluorescence, due to corrosion in the structure causes a fraction of the scattered light components to be reflected and returned by the gratings through the optic fiber in the opposite direction as the input signal. A two-way light coupler in the optical fiber diverts a portion of the reflected components for detection and display of the signature components from each grating as a function of intensity and cumulative corrosion.

Other objects, advantages and novel features of the invention will become apparent from the following detailed description of the invention when considered in conjunction with the accompanying claims.

DESCRIPTION OF THE PREFERRED EMBODIMENTS

Figure 1:
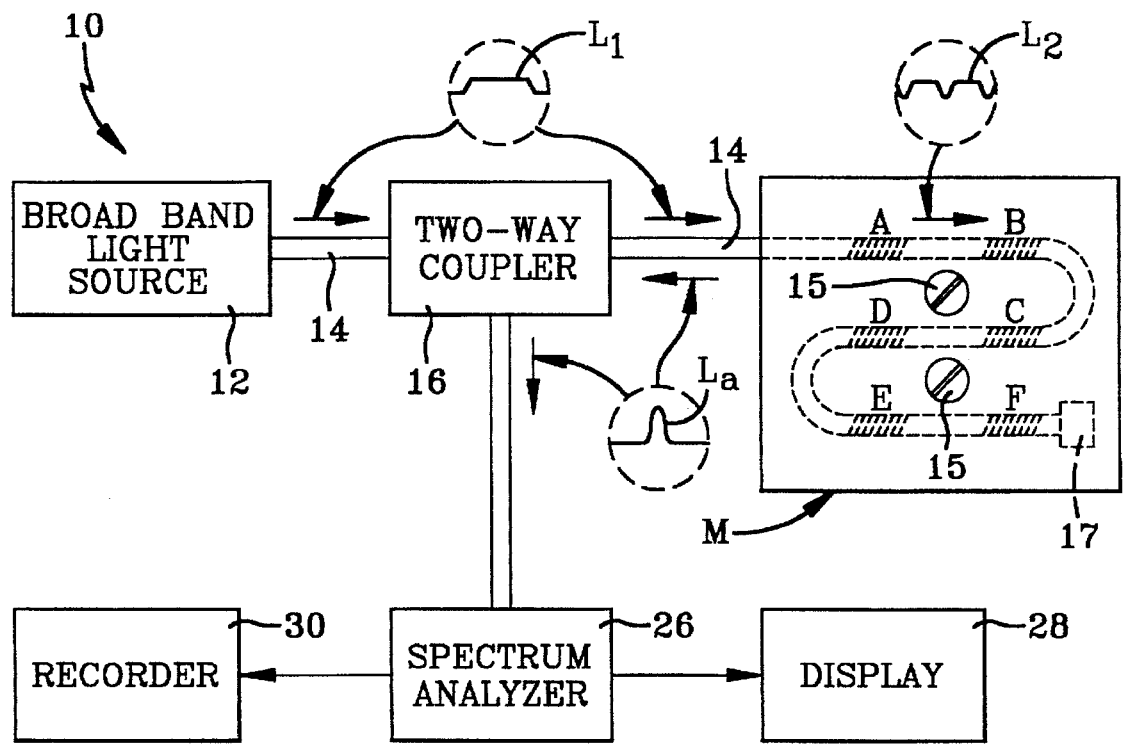
FIG. 1 is a schematic block diagram of a corrosion detecting and monitoring system with tapped Bragg gratings in an optical fiber sensor, according to the invention, embedded in a metal lap joint.

Referring now to the drawings wherein like reference characters denote like or corresponding parts throughout the several views, FIG. 1 shows an optical corrosion detecting and monitoring system, indicated generally by the numeral 10, as applied to a steel lap joint M. A light source 12 intermittently transmits a broad bandwidth light pulse $L_1$ in an optical fiber 14, which passes the frequencies unaltered through a two-way optical coupler 16, such a 3 dB coupler, to a series of tapped Bragg gratings A, B, C, D, E and F formed at selected spaced intervals in a distal segment of fiber 14 for embedment at sites of interest between opposed members $M_1$ and $M_2$ of a typical lap joint M with fasteners 15. A light absorber 17 at the distal end of optical fiber 14 prevents feedback or straying of any residual input signal.

Figures 2, 3:
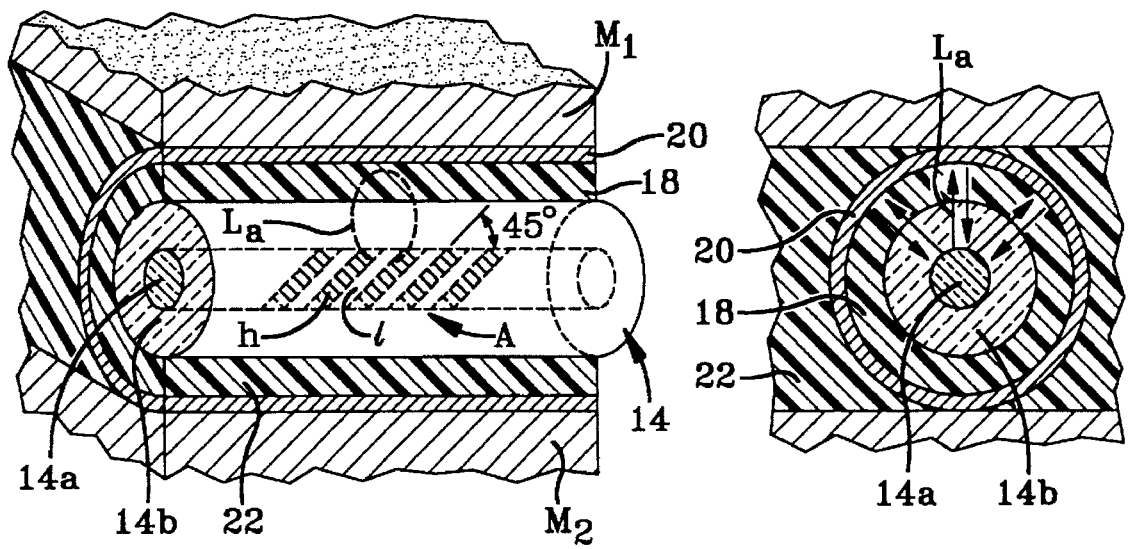
FIG. 2 is a cut-away view of the lap joint of FIG. 1 with a schematic representation of one tapped Bragg grating in a longitudinal segment of the optical fiber sensor.
FIG. 3 is a transverse cross-section of the lap joint and optical fiber sensor of FIG. 2.

As shown in FIGS. 2 and 3, optic fiber 14 is coated with a layer of compound 18 of a color responsive reduction/oxidation (redox) chemical either neat, or micro-encapsulated into a sparingly soluble methyl cellulose polymer and then silanized to protect the capsule walls from interaction with the solvents used in the coating foundation. Compound 18 is then completely surrounded by a non-continuous (perforated) metallic reflector 20 and finally the interstices are filled with a polyurethane to provide an environmental barrier coating 22. Compound 18 responds to corrosion due to changes in the environment and manifests itself as a change in color or fluorescence. The following table lists examples of redox color-responsive chemicals found suitable for detecting corrosion in alloys containing iron.

TABLE I

| Indicator Compound | Color Change | Redox Potential |
| --- | --- | --- |
| 1,10 Phenanthroline | Red to Faint Blue | 1.06 |
| 5-Nitro-1,10-Phenanthroline Ferrous Sulfate | Red to Faint Blue | 1.25 |
| 2,2-Bipyridyl Ferrous Sulfate | Red to Faint Blue | 0.97 |
| Ruthenium Tripyridyl Nitrate | Yellow-Colorless | 1.25 |
| Phenyl-2-Pyridyl Ketoxime Iron | Red to Colorless | N.A. |

The chemicals trigger a color response when in contact with ionic species Fe(II) which are the first ions produced during corrosion of steel. For instance, the transmission spectrum of Ferrorin (1,10 Phenan-throline-iron) is a function of the concentration of iron ions. Small amounts of the ions in a solution of this type can substantially increase the absorption behavior of the solution. As a result of a reduction-oxidation (redox) reaction, a clear coloration change is manifested from colorless (faint blue) to intense red or purple. The maximum absorption for this complex is in a narrow band region and in the visible spectrum, i.e. approximately 520 nm wavelength. Thus, the intensity of the color produced decreases as a function of corrosion.

A different corrosion-sensing scheme may be required for aluminum alloy structures because some of the chemicals do not form a colored complex with Al(III) ions. For this case, Columbia blue and fluorescein exhibit fluorescence chemicals when coupled with the aluminum ions exhibit fluorescence under ultraviolet light exposure.

Optical fiber 14 comprises a core 14a with an outer cladding 14b. Both the core and cladding are preferably made of silica, but a germanium (Ge) dopant is added to the silica core 14a to provide a slightly larger index of refraction. The difference in refraction indices confines the light input pulse $L_1$ to the core region.

The segment of core 14a in FIG. 2 schematically shows tapped Bragg grating A, and is representative of the construction of the other gratings B–F. The grating is made by placing the optical fiber at an approximate angle of 45° from the plane of an interference region of two orthagonal coherent light energy excimer laser beams thus forming a plurality of alternate planes of high and zero field intensities h and l slanted 45° from the axis of core 14a. The fields of high intensity h induce a change in the refraction index in core 14a due to small changes in the bonding properties of the Ge dopants present. As a result, periodic variations in the refraction indices are impressed along core 14a for each of gratings A–F.

The slanted intensity fields h and l in the interference region of grating A give off a spectral component $L_a$ of input signal $L_1$ approximately 90° from the axis of core 14a in a scattered fan-like pattern through cladding 14b and corrosion sensitive compound 18 to reflector 20. Depending upon the number of high intensity fields h in the interference region of each grating, the magnitude of change in refraction index from one grating to the next, and the spacing of the high intensity fields, a portion of spectral components $L_a$–$L_f$ tapped at each grating will be specularly returned by reflector 20 through the grating to two-way coupler 16 at a discrete spectral or "signature" component. The amplitude of each component is an indication of the amount of corrosion present adjacent to the respective gratings in lap joint M.

Reflector 20 may be omitted when compound 18 by itself provides sufficient corrosion response for detection.

The untapped portion of input signal $L_1$ represented by signal $L_2$, continues through grating A, to grating B where a different spectral component $L_b$ is tapped off and returned as described for component $L_a$. The remaining untapped portions of signal $L_2$ pass through gratings C, D, E, and F, each time tapping off and returning a spectral component $L_c$, $L_d$, $L_e$ or $L_f$.

Each tapped Bragg grating in optical fiber 14 is made with a different Bragg period $\Lambda_B$ so that they have unique "signature" narrow band widths that can be interrogated with a single broadband input pulse. The wavelength of the light pulse for the maximum sensitivity can be optimized by choosing the appropriate Bragg grating wavelength.

The number of tapped Bragg gratings placed on optical fiber 14 depends on the bandwidth of the input pulse and the bandwidth of each scattered spectral component. If the spectral bandwidth of the input pulse is sufficiently large compared to the bandwidth of the scattered spectral components, many unique "signature" Bragg gratings can be placed on a single optical fiber enabling interrogation of each individually. In the illustrated embodiment there are six gratings A–F each having a scattered spectral bandwidth of 200 nm, thereby requiring a broadband input pulse $L_1$ of white light with a bandwidth of 1200 nm. Other factors considered when fabricating the gratings are described in a paper incorporated by reference herein by I. Perez, V. Agarwala and W. R. Scott entitled *Bragg Grating Corrosion Sensor* presented on Jul. 31, 1995 at the Proceedings of the 19th Progress in Quantitative Nondestructive Evaluation, Iowa State University, July–August 1994.

Figure 4:
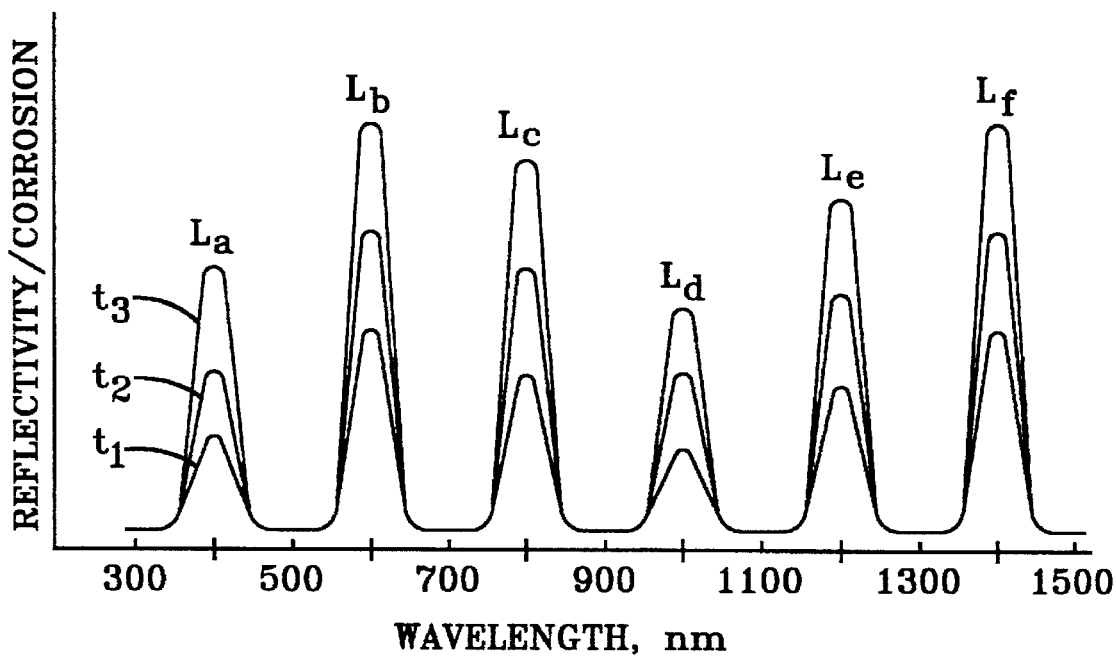
FIG. 4 graphically represents typical reflected scattered light pulses at different time intervals detected in the system of FIG. 1.
Figure 5:
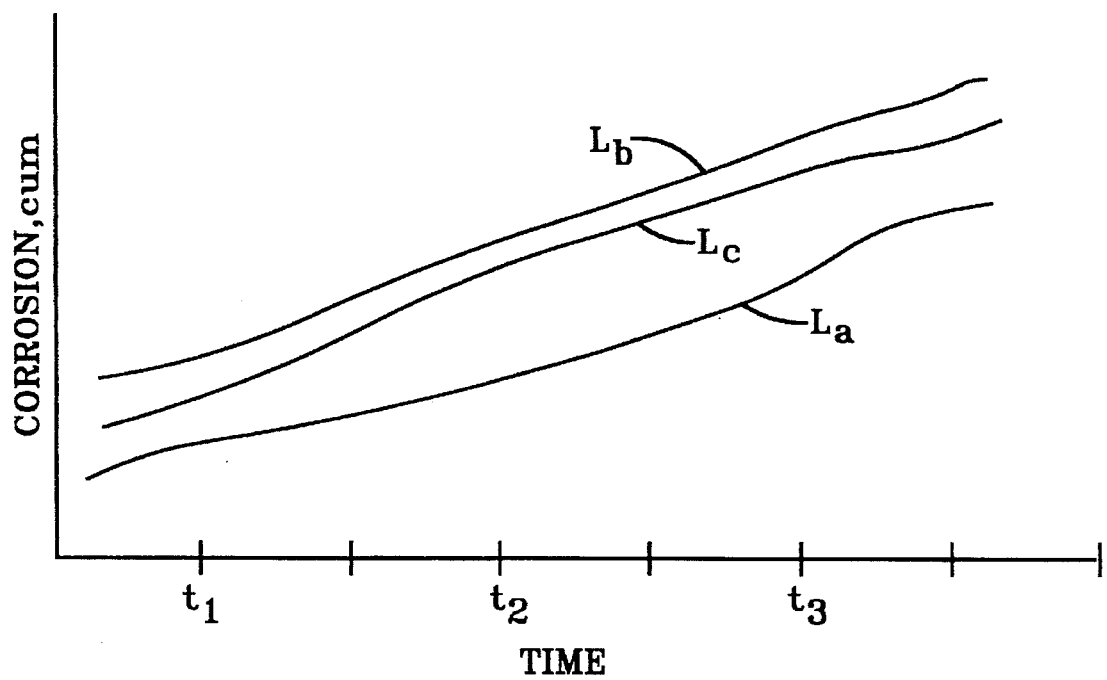
FIG. 5 graphically represents the cumulative corrosion of the lap joint at selected gratings of FIG. 4.

The spectral components $L_a$–$L_f$ tapped and reflected at each of gratings A–F are diverted by two-way optical coupler 16 to a spectrum analyzer 26 which transforms the light signals to an electrical output signal. The amplitude of each unique "signature" component from analyzer 26 appears at a display 28 as a measure of the respective gratings. FIG. 4 represents a typical display of three reflected narrow bandwidth components of each grating A–F measured at different intervals of time $t_1$, $t_2$ and $t_3$. A chart recorder 30 connected to an output of analyzer 26 displays the cumulative corrosion at gratings A, B and C over the interval between times $t_1$ and $t_3$.

Some of the many advantages and novel features of the invention should now be readily apparent. For example, the invention as herein described and claimed provides a nondestructive method and apparatus for detecting and monitoring the insidious effects of corrosion in structures which are normally inaccessible to observation. A single optic fiber can be installed in critical aircraft structure with tapped Bragg gratings located along the length of the fiber for detecting and measuring corrosion at multiple sites within the structure. The sensing element is very small, light weight, immune to electromagnetic interference and corrosion, and can be easily embedded or surface mounted on structure subject to corrosion.

It will be understood, of course, that various changes in the details, materials, steps and arrangement of parts, which have been herein described and illustrated in order to explain the nature of the invention, may be made by those skilled in the art within the principle and scope of the invention as expressed in the appended claims.

We claim:

1. Apparatus for nondestructive detection of corrosion in a structure comprising, in combination:

a light source for producing a broad bandwidth pulse;

an optical fiber having a proximal end connected to said light source for conducting said pulse in a direction through a distal segment of said optical fiber formed to be installed at a selected site on the structure;

a Bragg grating formed in said segment for refracting a narrow bandwidth component of the pulse from said fiber and a reflected amount of the component through said-fiber toward said light source;

sensor means applied to said fiber around said segment for reflecting a portion of the component toward said grating in response to corrosion of the structure at the selected site;

coupler means connected to said fiber between said light source and said grating for conducting a portion of the reflected amount from said fiber; and spectrum analyzer means connected to said coupler means for receiving said portion and determining the amplitude distribution of the reflected amount in the narrow bandwidth; and display means connected to said analyzer means for producing a graph of the reflected amount indicative of the corrosion at the selected site.

2. Apparatus according to claim 1 wherein said Bragg grating comprises:

an interference region in a plane approximately 45° from the optical fiber axis.

3. Apparatus according to claim 2 wherein said grating has a Bragg period for refracting a predetermined narrow bandwidth of the broad bandwidth pulse.

4. Apparatus according to claim 1 wherein said sensor includes a redox chemical coating responsive to changes in color in the presence of corrosion at the selected site.

5. Apparatus according to claim 4 wherein said sensor means includes a partial reflector surrounding said coating for returning the reflected amount of the component.

6. Apparatus according to claim 4 wherein said chemical is of the group consisting of 1,10 phenanthroline, 5-nitro-1,10-phenanthroline ferrous sulfate, 2,2-bipyridyl ferrous sulfate, ruthenium tripyridyl nitrate, and phenyl-2-pyridyl ketoxime iron.

7. Apparatus according to claim 4 wherein said chemical is of the group consisting of columbia blue and fluorescein.

8. Apparatus according to claim 1 wherein said optical fiber includes a core and cladding of silica, and a dopant in said core producing a greater index of refraction therein than said cladding for confining the pulse within said core.

9. Apparatus for nondestructive detection of corrosion in a structure comprising, in combination:

a light source for producing a broad bandwidth pulse;

an optical fiber having a proximal end connected to said light source for conducting said pulse in a direction through a distal segment of said optic fiber formed to be installed at selected sites on the structure;

a plurality of Bragg gratings formed in said segment at spaced intervals for refracting components of different narrow bandwidths of the pulse from said fiber and reflected amounts of the components through said fiber toward said light source;

sensor means applied to said fiber around said segment for reflecting portions of the components toward said gratings in response to corrosion of the structure at the respective selected sites;

coupler means connected to said fiber between said light source and said gratings for conducting portions of the reflected amounts from said fiber;

spectrum analyzer means connected to said coupler means for receiving said portions and determining the amplitude distribution of the reflected amounts in each narrow bandwidth; and display means connected to said analyzer means for producing a graph of the reflected amounts indicative of the corrosion at the respective selected sites.

10. Apparatus according to claim 9 wherein each of said Bragg gratings comprises:

an interference region in a plane approximately 45° from the optic fiber axis.

11. Apparatus according to claim 10 wherein each of said grating has a Bragg period for refracting a different predetermined narrow bandwidth of the broad bandwidth pulse.

12. A method of detecting corrosion in a structure comprising the steps of:

installing a distal segment of an optic fiber in the structure, said segment containing a series of Bragg gratings having different refraction indexes encapsulated in a redox chemical responsive to changes in color or fluorescence with increases in corrosion;

providing a broad bandwidth pulse to the proximal end of the optical fiber;

diverting reflected components of narrow bandwidths received from each of said gratings; and sensing the amplitude distribution of each of said diverted reflected components in the narrow bandwidths.

* * * * *